United States Patent [19]

Kajihara et al.

[11] Patent Number: 4,904,405
[45] Date of Patent: Feb. 27, 1990

[54] AEROSOL PREPARATIONS CONTAINING MIXTURES OF PHOSPHATE ESTERS

[75] Inventors: Yasushi Kajihara, Kasukabe; Noriyoshi Fujisawa, Sakura; Masatoshi Arisawa, Matsudo, all of Japan

[73] Assignee: Kao Corporation, Tokyo, Japan

[21] Appl. No.: 316,942

[22] Filed: Feb. 28, 1989

[30] Foreign Application Priority Data

Feb. 29, 1988 [JP] Japan .................................. 63-47020

[51] Int. Cl.$^4$ .................. C11D 17/00; C11D 1/34
[52] U.S. Cl. .................. 252/90; 252/174.16; 252/545; 252/DIG. 14; 252/DIG. 17
[58] Field of Search .......... 252/174.16, 545, DIG. 17, 252/90

[56] References Cited

U.S. PATENT DOCUMENTS

| | | | |
|---|---|---|---|
| 4,049,558 | 9/1977 | Rasmussen | 252/8.9 |
| 4,132,679 | 1/1979 | Tsutsumi et al. | 252/545 |
| 4,139,485 | 2/1979 | Imokawa et al. | 252/135 |
| 4,259,204 | 3/1981 | Homma | 252/174.16 |
| 4,298,494 | 11/1981 | Parslow | 252/174.16 |
| 4,363,755 | 12/1982 | Uchino et al. | 252/545 |
| 4,369,134 | 1/1983 | Deguchi et al. | 252/526 |
| 4,381,259 | 4/1983 | Homma et al. | 252/542 |
| 4,479,893 | 10/1984 | Hirota et al. | 252/542 |
| 4,574,052 | 3/1986 | Gupte et al. | 252/90 |
| 4,707,292 | 11/1987 | Sano et al. | 252/174.16 |

FOREIGN PATENT DOCUMENTS

| | | |
|---|---|---|
| 16481 | 5/1907 | Japan . |
| 101197 | 6/1983 | Japan . |
| 224194 | 6/1987 | Japan . |
| 2199700 | 9/1987 | Japan . |
| 2139112 | 11/1984 | United Kingdom . |

OTHER PUBLICATIONS

Patent Abstracts of Japan, vol. 9, No. 5, Jan. 10, 1985, JP-A-59 161 309.

*Primary Examiner*—Prince E. Willis
*Attorney, Agent, or Firm*—Oblon, Spivak, McClelland, Maier & Neustadt

[57] ABSTRACT

An aerosol preparation containing a cleansing agent and a propellant is provided. The cleansing agent is composed of a phosphate ester surfactant obtained by mixing two alkylphosphate salts a weight ratio of from 70:30 to 20:80. The first alkylphosphate salt is represented by:

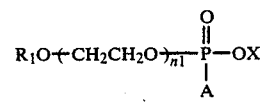

wherein $R_1$ means a $C_{12-14}$ hydrocarbon group, X denotes a specific cation, n1 is 0–10, A is $R_2O$—$CH_2CH_2O)_{n2}$ or —OY, $R_2$ having the same meaning as $R_1$, Y denoting a specific cation, and n2 being a value of 0–10. The second alkylphosphate salt is represented by:

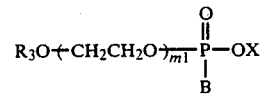

wherein $R_3$ is similar to $R_1$ and $R_2$ except for inclusion of more carbon atoms, m1 is 0–10, B denotes $R_4O$—$CH_2CH_2O)_{m2}$ or —OY, $R_4$ having the same meaning as $R_3$, m2 being 0–10 and Y having the same meaning as defined above, X has the same meaning as defined above.

3 Claims, No Drawings

AEROSOL PREPARATIONS CONTAINING MIXTURES OF PHOSPHATE ESTERS

BACKGROUND OF THE INVENTION (1) Field of the Invention

This invention relates to novel aerosol preparations, and more specifically to aerosol preparations satisfactory in both foamability and foam stability and useful as skin cleansing preparations such as shaving preparations.

(2) Description of the Related Art

In recent years, there is an ever-increasing safety demand for various cleansing preparations. Alkylphosphate salts have thus been developed as surfactants having high safety and are used in solid cleansing preparations, shampoos, dentifrices, etc.

Among such alkylphosphate esters, laurylphosphate salts and myristylphosphate salts are superior as skin cleansing surfactants, primarily, from the standpoint of foaming power. Palmitylphosphate salts, stearylphosphate salts and the like have not been used because they have substantially no foaming power.

Where a skin cleansing preparation is in the form of an aerosol preparation such as a shaving foam, good foam stability is also required along with high foamability. Use of an alkylphosphate salt having good foamability such as a laurylphosphate salt is accompanied by a drawback that the stability of foams is poor.

SUMMARY OF THE INVENTION

The present inventors have carried out an extensive investigation with a view toward developing foam-type aerosol preparations, which are mild to the skin and have high stability, by using a surfactant of the alkylphosphate salt type. As a result, it has been found surprisingly that skin cleansing preparations of the aerosol foam type, which are excellent in both foamability and stability, can be obtained by adding a low-foamability alkylphosphate salt such as palmitylphosphate salt or stearylphosphate salt to a high-foamability alkylphosphate salt such as laurylphosphate salt, leading to completion of this invention.

In one aspect of this invention, there is thus provided an aerosol preparation comprising:

a cleansing agent comprising a phosphate ester surfactant obtained by mixing (A) a first alkylphosphate salt represented by the following formula (I):

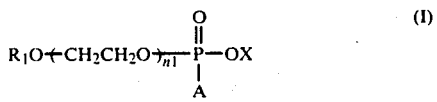

wherein $R_1$ means a saturated or unsaturated hydrocarbon group having 12-14 carbon atoms, X denotes a hydrogen atom, alkali metal, ammonium or alkanolamine having 2-3 carbon atoms, n1 stands for a value of 0-10, A is $R_2O\text{-}(CH_2CH_2O)_{n2}$ or $-OY$, $R_2$ meaning a saturated or unsaturated hydrocarbon group having 12-14 carbon atoms, Y denoting a hydrogen atom, alkali metal, ammonium or alkanolamine having 2-3 carbon atoms and n2 being a value of 1-10, and the weight ratio of monoalkyl ester to dialkyl ester is from 100/0 to 50/50, with (B) a second alkylphosphate salt represented by the following formula (II):

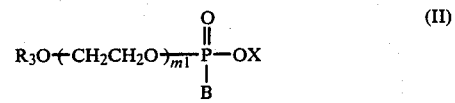

wherein $R_3$ means a saturated or unsaturated hydrocarbon group having 16-18 carbon atoms, m1 stands for a value of 0-10, B denotes $R_4O\text{-}(CH_2CH_2O)_{m2}$ or $-OY$, $R_4$ meaning a saturated or unsaturated hydrocarbon group having 16-18 carbon atoms, m2 being a value of 0-10 and Y having the same meaning as defined above, X has the same meaning as defined above, and the weight ratio of monoalkyl ester to dialkyl ester is from 100/0 to 50/50, at a weight ratio of the first alkylphosphate salt (A) to the second alkylphosphate salt (B) of from 70:30 to 20:80; and a propellant in a proportion of 1-80 parts by weight per 100 parts by weight of the cleansing agent.

The cleansing agent has good foamability and also good stability. The aerosol preparation of this invention, which makes use of this cleansing agent, has inherited the above good properties of the cleansing agent. The aerosol preparation is hence useful, for example, as a shaving foam, face washing foam, foam shampoo, body washing foam or pet washing foam.

DETAILED DESCRIPTION OF THE INVENTION AND PREFERRED EMBODIMENTS

The first alkylphosphate salt as the component (A) in the preparation according to this invention is a mixture of monoalkylphosphate salt and dialkylphosphate salt, both, represented by the formula (I). As $R_1$ and $R_2$ in the alkylphosphate salt (I), linear hydrocarbon groups are preferred. Dodecyl, tridecyl and tetradecyl groups and their corresponding unsaturated groups may be mentioned by way of example. $R_1$ and $R_2$ may each be a single hydrocarbon group or a combination of plural hydrocarbon groups. Saturated hydrocarbon groups having an average carbon number of 12 are preferred. Further, alkylphosphate salts of the formula (I) in which n1 and n2 are both 0 are preferred. Potassium or ethanolamine or the like is preferred as the counter ions represented by X and Y.

In the first alkylphosphate salt of the formula (I), the mixing ratio of monoalkyl ester to dialkyl ester may preferably be from 100/0 to 80/20 by weight.

On the other hand, the second alkylphosphate salt as the component (B) is a mixture of monoalkylphosphate salts and dialkylphosphate salt, both, represented by the formula (II). As $R_3$ and $R_4$ in the alkylphosphate salt (II), linear hydrocarbon groups are preferred. Pentadecyl, hexadecyl, heptadecyl and octadecyl and their corresponding unsaturated groups may be mentioned by way of example. In particular, saturated hydrocarbon groups having an average carbon number of 16 are preferred. Further, alkylphosphate salts of the formula (II) in which m1 and m2 are both 0 are preferred. Potassium or ethanolamine or the like is preferred as the counter ions represented by X and Y.

In the second alkylphosphate salt of the formula (II), the mixing ratio of monoalkyl ester to dialkyl ester may preferably be from 100/0 to 80/20 by weight.

To formulate a phosphate ester surfactant from the above components (A) and (B), it is only necessary to mix them to give an (A):(B) weight ratio of from 70:30 to 20:80. Of these, phosphate ester surfactants having an (A):(B) weight ratio in a range of from 70:30 to 40:60 have excellent stability. This phosphate ester surfactant may be incorporated, preferably, in an proportion of 1–50 wt.% (hereinafter referred to "%" for the sake of brevity), notably, 5–20%.

On the other hand, illustrative examples of the propellant may generally include halogenated hydrocarbons such as dichlorodifluoromethane, chlorodifluoroethane, chlorodifluoromethane and trichlorotrifluoroethane; hydrocarbons having 1–6 carbon atoms such as propane, n-butane and isopentane; and compressed gases such as liquefied petroleum gas, dimethyl ether, nitrogen gas, nitrogen dioxide gas and carbon dioxide gas.

These propellants may be incorporated preferably in a proportion of 1–80 parts by weight, notably, 1–20 parts by weight per 100 parts by weight of the cleansing agent comprising the phosphate ester surfactant, and at 2–7 kg/cm$^2$–G (at 25° C.).

The cleansing preparation according to this invention can be formulated by mixing the phosphate ester surfactant and propellant in a manner known per se in the art. It is preferable to adjust the pH of the preparation to 6.5–8.5, as measured in the form of a 5% aqueous solution, in view of foamability and skin irritation. The neutralization equivalent of each of the first and second alkylphosphate salts, namely, the molar ratio of a base to be required to neutralize each of the first and second alkylphosphate salts may be 1.0–1.8, with a range of 1.2–1.5 being preferred. In such a case, it is most suitable that the weight ratio of the component (A) to the component (B) falls within a range of from 70/30 to 40/60. Besides the essential components described above, the cleansing preparation according to this invention may contain, depending on its form and application purpose, one or more of solvents such as water, colors, perfume bases, antiseptics, antiphlogistics, chelating agents, inorganic and organic salts, viscosity modifiers, foaming intensifiers, preservatives, moisturizing agents and various other surfactants to extents not impairing effects of the present invention.

The present invention will hereinafter be described in further detail by the following Examples. It should however be borne in mind that the present invention is not necessarily be limited thereto.

EXAMPLE 1

Aerosol preparations were prepared by mixing a laurylphosphate salt and a palmitylphosphate salt at various ratios, and their foamability and foam stability were investigated. Investigation results are summarized in Table 1.

| (Composition of the aerosol preparations) | |
| --- | --- |
| Potassium monolaurylphosphate* | 10(%) |
| Potassium monopalmitylphosphate* | |
| Water | 85 |
| LPG (5.0 kg/cm$^2$-G) | 5 |

*Neutralization equivalent: 1.3

TABLE 1

| Weight ratio of potassium monolaurylphosphate to potassium monopalmityl phosphate | Foam* stability (min) |
| --- | --- |
| 100/0 | 1 |
| 90/10 | 2 |
| 80/20 | 4 |
| 70/30 | 48 |
| 60/40 | 76 |
| 50/50 | 90 |
| 40/60 | 73 |
| 30/70 | 30 |
| 20/80 | 28 |
| 10/90 | 7 |
| 0/100 | 5 |

*Evaluation standard: Foams were jetted out in the form of a ball having a diameter of 4 cm. The time required until the foam height lowered to one half was recorded as a value of foam stability.

EXAMPLE 2

Aerosol preparations were formulated by mixing laurylphosphate and palmitylphosphate of various neutralization equivalents at a ratio of 1:1, and their foamability and foam stability were investigated. Investigation results are summarized in Table 2.

| (Composition of the aerosol preparations) | |
| --- | --- |
| Monolaurylphosphate | 5.0(%) |
| Monopalmitylphosphate | 5.0 |
| KOH (As needed for neutralization, see Table 2) | |
| LPG (5.0 kg/cm$^2$-G) | 5.0 |
| Water | to 100 |

TABLE 2

| Neutralization equivalent | Foam stability |
| --- | --- |
| 1.2 | 76 |
| 1.3 | 90 |
| 1.4 | 83 |
| 1.5 | 66 |

EXAMPLE 3

Using various phosphate ester salts, aerosol preparations were formulated. The foam stability of the aerosol preparations was investigated. Investigation results are summarized in Table 3.

| (Composition of the aerosol preparations) | |
| --- | --- |
| Potassium salt of phosphate ester* | 10.0(%) |
| Water | 85.0 |
| LPG (5.0 kg/cm$^2$-G) | 5.0 |

*Neutralization equivalent: 1.3

TABLE 3

| Potassium salt of phosphate ester | Wt. % | Foam stability |
| --- | --- | --- |
| Potassium laurylphosphate[1] | 5.0 | 72 |
| Potassium monopalmitylphosphate | 5.0 | |
| Potassium polyoxyethylene laurylether phosphate (3E.O)[2] | 5.0 | 75 |
| Potassium monopalmitylphosphate | 5.0 | |
| Potassium laurylphosphate[3] | 5.0 | 68 |
| Potassium palmitylphosphate[4] | 5.0 | |

[1]–[4] Monoalkyl ester content: 85%

We claim:

1. An aerosol preparation comprising:

a cleansing agent comprising a phosphate ester surfactant obtained by mixing (A) a first alkylphosphate salt represented by the following formula (I):

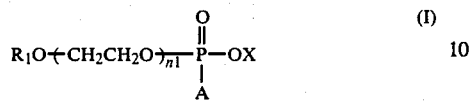

wherein $R_1$ means a saturated or unsaturated hydrocarbon group having 12–14 carbon atoms, X denotes a hydrogen atom, alkali metal, ammonium or alkanolamine having 2–3 carbon atoms, n1 stands for a value of 0–10, A is $R_2O \!-\!\!(CH_2CH_2O)_{\overline{n2}}$ or $-OY$, $R_2$ meaning a saturated or unsaturated hydrocarbon group having 12–14 carbon atoms, Y denoting a hydrogen atom, alkali metal, ammonium or alkanolamine having 2–3 carbon atoms and n2 being a value of 0–10, and the weight ratio of monoalkyl ester to dialkyl ester is from 100/0 to 50/50, with (B) a second alkylphosphate salt represented by the following formula (II):

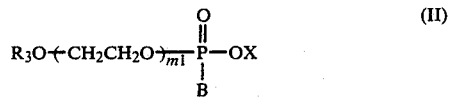

wherein $R_3$ means a saturated or unsaturated hydrocarbon group having 16–18 carbon atoms, m1 stands for a value of 0–10, B denotes $R_4O \!-\!\!(CH_2CH_2O)_{\overline{m2}}$ or $-OY$, $R_4$ meaning a saturated or unsaturated hydrocarbon group having 16–18 carbon atoms, m2 being a value of 0–10 and Y having the same meaning as defined above, X has the same meaning as defined above, and the weight ratio of monoalkyl ester to dialkyl ester is from 100/0 to 50/50, at a weight ratio of the first alkylphosphate salt (A) to the second alkylphosphate salt (B) of from 70:30 to 20:80; and a propellant in a proportion of 1–80 parts by weight per 100 parts by weight of the cleansing agent.

2. The aerosol preparation as claimed in claim 1, wherein the neutralization equivalent of each of the first and second alkylphosphate salts (A) and (B) is in a range of from 1.0 to 1.8.

3. The aerosol preparation as claimed in claim 1, wherein the neutralization equivalent of each of the first and second alkylphosphate salts (A) and (B) is in a range of from 1.2 to 1.5 and the weight ratio of the first alkyl phosphate salt (A) to the second alkyl phosphate salt (B) is from 70:30 to 40:60.

* * * * *